United States Patent
De Wilde et al.

(10) Patent No.: US 9,226,830 B2
(45) Date of Patent: Jan. 5, 2016

(54) DEVICE AND METHOD FOR RETROVERSION CORRECTION FOR SHOULDER ARTHROPLASTY

(75) Inventors: Lieven De Wilde, Ghent (BE); Kyle Lappin, Ft Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 785 days.

(21) Appl. No.: 13/051,041

(22) Filed: Mar. 18, 2011

(65) Prior Publication Data

US 2012/0239051 A1    Sep. 20, 2012

(51) Int. Cl.
| | |
|---|---|
| A61F 2/40 | (2006.01) |
| A61F 2/30 | (2006.01) |
| A61B 17/17 | (2006.01) |

(52) U.S. Cl.
CPC ....... *A61F 2/4081* (2013.01); *A61B 2017/1778* (2013.01); *A61F 2002/3023* (2013.01); *A61F 2002/30736* (2013.01); *A61F 2002/30769* (2013.01); *A61F 2002/30881* (2013.01); *A61F 2002/30892* (2013.01)

(58) Field of Classification Search
CPC ..................................... A61F 2/40–2002/4085
USPC .......... 623/19.11–19.14, 20.22, 21.13, 21.15, 623/21.16; 606/96; 62/19.11–19.14
See application file for complete search history.

(56) References Cited

U.S. PATENT DOCUMENTS

| | | | |
|---|---|---|---|
| 2,487,203 A | 11/1949 | Wilber | |
| 3,855,638 A | 12/1974 | Pilliar | |
| 4,030,143 A | 6/1977 | Elloy et al. | |
| 4,964,865 A * | 10/1990 | Burkhead et al. | 623/19.11 |
| 5,030,219 A | 7/1991 | Matsen, III et al. | |
| 5,080,673 A | 1/1992 | Burkhead et al. | |
| 5,180,384 A | 1/1993 | Mikhail | |
| 5,324,295 A | 6/1994 | Shapiro | |
| 5,489,310 A * | 2/1996 | Mikhail | 623/19.11 |
| 5,800,551 A * | 9/1998 | Williamson et al. | 623/19.11 |
| 5,919,195 A | 7/1999 | Wilson et al. | |

(Continued)

FOREIGN PATENT DOCUMENTS

| | | |
|---|---|---|
| CH | 693446 A5 | 8/2003 |
| EP | 1639949 A1 | 3/2006 |

(Continued)

OTHER PUBLICATIONS

Bey, Michael J., et al., "Measuring Dynamic In-Vivo Glenohumeral Joint Kinematics: Technique and Preliminary Results," Journal of Biomechanics 41 (2008), pp. 711-714. (4 pages).

(Continued)

*Primary Examiner* — Christopher D Prone
(74) *Attorney, Agent, or Firm* — Maginot, Moore & Beck, LLP (57) ABSTRACT

A kit for implanting a glenoid component in one embodiment includes a retroversion glenoid component including a generally flat glenoid bone contacting surface defining a first plane, a first offset peg extending away from the glenoid bone contacting surface, a concave articulating surface, an upper surface extending about the concave articulating surface and generally opposite to the glenoid bone contacting surface, the upper surface defining a second plane, the second plane angled with respect to the first plane, and a drill guide configured to guide a drill in forming a bore in a scapula to receive the first offset peg.

20 Claims, 9 Drawing Sheets

(56) References Cited

U.S. PATENT DOCUMENTS

| | | | |
|---|---|---|---|
| 6,045,302 A | 4/2000 | Orr | |
| 6,228,900 B1 | 5/2001 | Shen et al. | |
| 6,245,074 B1 | 6/2001 | Allard et al. | |
| 6,281,264 B1 | 8/2001 | Salovey et al. | |
| 6,364,910 B1* | 4/2002 | Shultz et al. | 623/19.11 |
| 6,379,386 B1 | 4/2002 | Resch et al. | |
| 6,679,916 B1 | 1/2004 | Frankle et al. | |
| 6,699,289 B2 | 3/2004 | Iannotti et al. | |
| 6,783,549 B1 | 8/2004 | Stone et al. | |
| 7,294,133 B2 | 11/2007 | Zink et al. | |
| 7,329,284 B2 | 2/2008 | Maroney et al. | |
| 7,338,498 B2 | 3/2008 | Long et al. | |
| 7,604,665 B2 | 10/2009 | Iannotti et al. | |
| 8,764,836 B2 | 7/2014 | De Wilde et al. | |
| 2002/0082702 A1* | 6/2002 | Resch et al. | 623/19.11 |
| 2003/0125809 A1* | 7/2003 | Iannotti et al. | 623/19.13 |
| 2004/0097947 A1 | 5/2004 | Wolford et al. | |
| 2004/0193168 A1 | 9/2004 | Long et al. | |
| 2005/0278030 A1 | 12/2005 | Tornier et al. | |
| 2006/0015112 A1 | 1/2006 | McGovern | |
| 2006/0020344 A1 | 1/2006 | Shultz et al. | |
| 2006/0069444 A1 | 3/2006 | Deffenbaugh | |
| 2006/0111787 A1 | 5/2006 | Bailie et al. | |
| 2006/0195194 A1 | 8/2006 | Gunther | |
| 2006/0276905 A1* | 12/2006 | Calamel | 623/22.28 |
| 2007/0016304 A1 | 1/2007 | Chudik | |
| 2007/0038302 A1 | 2/2007 | Shultz et al. | |
| 2007/0055249 A1 | 3/2007 | Jensen et al. | |
| 2007/0251356 A1 | 11/2007 | Tribby | |
| 2007/0260321 A1 | 11/2007 | Stchur | |
| 2008/0306600 A1 | 12/2008 | Huebner | |
| 2009/0270993 A1 | 10/2009 | Maisonneuve et al. | |
| 2010/0070044 A1 | 3/2010 | Maroney et al. | |
| 2010/0087876 A1 | 4/2010 | Gunther | |
| 2010/0161065 A1 | 6/2010 | Williams, Jr. et al. | |
| 2010/0274359 A1 | 10/2010 | Brunnarius et al. | |
| 2010/0331990 A1 | 12/2010 | Mroczkowski et al. | |
| 2011/0028977 A1 | 2/2011 | Rauscher et al. | |
| 2011/0035013 A1 | 2/2011 | Winslow et al. | |
| 2012/0130499 A1* | 5/2012 | Long | 623/19.11 |
| 2013/0123930 A1 | 5/2013 | Burt | |

FOREIGN PATENT DOCUMENTS

| | | |
|---|---|---|
| EP | 1815825 A1 | 8/2007 |
| FR | 2704747 A1 | 11/1994 |
| FR | 2940607 A1 | 7/2010 |
| GB | 2406278 A | 3/2005 |
| WO | 2011005205 A1 | 1/2011 |

OTHER PUBLICATIONS

Chant, Chris B., et al., "Humeral Head Retroversion in Competitive Baseball Players and Its Relationship to Glenohumeral Rotation Range of Motion," Journal of Orthopaedic & Sports Physical Therapy, Sep. 2007, vol. 37, No. 9, pp. 514-520. (7 pages).

Conzen, Annemarie and Eckstein, Felix, MD, "Quantitative Determination of Articular Pressure in the Human Shoulder Joint," Journal of Shoulder and Elbow Surgery, vol. 9, No. 3, May/Jun. 2000, pp. 196-204. (9 pages).

De Wilde, Lieven F. MD, et al., "Glenohumeral Relationship in the Transverse Plane of the Body," Journal of Shoulder and Elbow Surgery, vol. 12, No. 3, May/Jun. 2003, pp. 260-267. (8 pages).

De Wilde, L.F., et al., "About the Variability of the Shape of the Glenoid Cavity," Surgical and Radiologic Anatomy (2004) 26; pp. 54-59. (6 pages).

Fleiss, Joseph L., "Analysis of Data From Multiclinic Trials," Controlled Clinical Trials 7: 267-275 (1986). (9 pages).

Hertel, Ralph M.D., "Geometry of the Proximal Humerus and Implications for Prosthetic Design," Journal of Shoulder and Elbow Surgery, Jul./Aug. 2002, vol. 11, No. 4, pp. 331-338. (8 pages).

Mansat, M. and Fourcade, D., "Preoperative Planning in Shoulder Prosthesis," Acta Orthopaedica Belgica (1995) vol. 61-Suppl. Jan. 1995. (6 pages).

Middernacht, Bart, MD, et al., "Consequences of Scapular Anatomy for Reversed Total Shoulder Arthroplasty,"Clinical Orthopaedics and Related Research (2008) 466: 1410-1418. (9 pages).

Moon, P. and Spencer, D.E., Rectangular Coordinates (x,y,z). Field Theory Handbook, Including Coordinate Systems, Differential Equations, and Their Solutions (1988), New York: Springer-Verlag, pp. 9-11 (Table 1.01). (3 pages).

Pearl, Michael L., M.D. and Volk, Albert G., M.D., "Coronal Plane Geometry of the Proximal Humerus Relevant to Prosthetic Arthroplasty," Journal of Shoulder and Elbow Surgery, vol. 5, No. 4, Jul./Aug. 1996, pp. 320-326. (7 pages).

Pearl, ML and Volk, AG, "Retroversion of the Proximal Humerus in Relationship to Prosthetic Replacement Arthroplasty," Journal of Shoulder and Elbow Surgery, Jul. 1995, vol. 4, No. 4, pp. 286-289. (4 pages).

Randelli, M., M.D. and Gambrioli, P.L., M.D., "Glenohumeral Osteometry by Computed Tomography in Normal and Unstable Shoulders," Clinical Orthopaedics and Related Research, No. 208, Jul. 1986, pp. 151-156. (6 pages).

Robertson, Douglas D., M.D., et al., "Three-Dimensional Analysis of the Proximal Part of the Humerus: Relevance to Arthroplasty," The Journal of Bone and Joint Surgery, vol. 82-A,No. 11, Nov. 2000, pp. 1594-1602. (9 pages).

Rougraff, Bruce T., M.D., et al., "Does Length of Symptoms Before Diagnosis of Sarcoma Affect Patient Survival?" Clinical Orthopaedics and Related Research (2007), No. 462, pp. 181-189. (9 pages).

Shrout, Patrick E. and Fleiss, Jospeh L., "Intraclass Correlations: Uses in Assessing Rater Reliability," Psychological Bulletin, 1979, vol. 86, No. 2, pp. 420-428. (9 pages).

Soslowsky, Louis J., Ph.D. et al, "Articular Geometry of the Glenohumeral Joint," Clinical Orthopaedics and Related Research, No. 285, Dec. 1992, pp. 181-190. (10 pages).

Tetreault, Patrice, et al., "Glenoid Version and Rotator Cuff Tears," Journal of Orthopaedic Research 22 (2004) pp. 202-207. (6 pages).

Warner, Jon J.P., M.D. et al, "Articular Contact Patterns of the Normal Glenohumeral Joint," Journal of Shoulder and Elbow Surgery, Jul./Aug. 1998, vol. 7, No. 4, pp. 381-388. ( 8 pages).

Westerhoff, P., et al., "In Vivo Measurement of Shoulder Joint Loads During Activities of Daily Living," Journal of Biomechanics 42 (2009), pp. 1840-1849. (10 pages).

Williams, Gerald R., Jr., M.D., and Iannotti, Joseph P., M.D. PhD., "Options for Glenoid Bone Loss: Composites of Prosthetics and Biologics," Journal of Shoulder and Elbow Surgery, Sep./Oct. 2007, vol. 16, No. 5S, pp. 267S-272S. (6 pages).

Wirth, Michael A., M.D. and Rockwood, Charles A., Jr., M.D., "Complications of Shoulder Arthroplasty," Clinical Orthopaedics and Related Research, Oct. 1994, No. 307, pp. 47-69. ( 23 pages).

Wirth, Michael A. and Rockwood, Charles A., Jr., "Current Concepts Review—Complications of Total Shoulder-Replacement Arthroplasty," Journal of Bone & Joint Surgery, Apr. 1996, vol. 78-A, No. 4, pp. 603-616. (15 pages).

Jeske, H.C. et al., "Normal glenoid rim anatomy and the reliability of shoulder instability measurements based on intrasite correlation," Surg. Radiol. Anat., vol. 31, pp. 623-625, Mar. 2009 (3 pages).

International Search Report in corresponding PCT Application (i.e., PCT/US2012/029021), mailed Jul. 11, 2012 (4 pages).

Antuna et al., "Glenoid revision surgery after total shoulder arthroplasty," Journal of Shoulder Elbow Surgery, 2001, pp. 217-224, vol. 10, Rochester, MN (8 pages).

Boileau P, Walch G., "The three dimensional geometry of the proximal humerus. Implications for the surgical technique and prosthetic design." J. Bone Joint Surg Br 1997;79-B:857-65. doi:10.1302/0301-620X.79B5.7579 (9 pages).

Boyer PJ, Massimini DF, Gill TJ, Papannagari R, Stewart SL, Warner JP, Li G., "In vivo articular cartilage contact at the glenohumeral joint: preliminary report." J. Orthop Sci. 2008;13:359-65.doi:10. 1007/s00776-008-1237-3 (7 pages).

Bryce CD, Davison AC, Lewis GS, Wang, Flemming DJ, Armstrong AD., "Two dimensional glenoid version measurements vary with coronal and sagittal scapular rotation." J Bone Joint Surg Am. 2010;92-692-9.doi.10.2106/ JBJS.I.00177 (8 pages).

(56) References Cited

OTHER PUBLICATIONS

Codsi et al., "Normal glenoid vault anatomy and validation of a novel glenoid implant shape," Journal of Shoulder Elbow Surgery, May/Jun. 2008, pp. 471-478, vol. 17, Austria (8 pages).
Couteau B, Mansat, Darmana R, Mansat M., Egan J., "Morphological and mechanical analysis of the glenoid by 3D geometric reconstruction using computed tomography." Clin Biomech 2000;15(suppl1):8-12.doi:10.1016/50268-0033(00)00052-8 (5 pages).
Couteau B, Mansat P. Estivales E, Darmana R. Mansat M., Egan J., "Finite element analysis of the mechanical behavior of a scapula implanted with a glenoid prosthesis." Clin Biomech 2001;16:566-75. doi:10.1016/50268-0033(01)00029-8 (10 pages).
Couteau B, Mansat P, Mansat M, Darmana R, Egan J., "In vivo characterization of glenoid with use of computed tomography." J Shoulder Elbow Surg 2001;116-22 (7 pages).
De Wilde LF, Verstraeten T, Speeckaert W, Karelse A., "Reliability of the glenoid plane." J Shoulder Elbow Surg. 2010;19:414-22. doi:10.1016/j.jse.2009.10.005. (9 pages).
Graichen H, Hinterwimmer S, von Eisenhart-Rothe R, Vogl T. Englmeier KH, Eckstein F., "Effect of abducting and adducting muscle acitivity on glenohumeral translation, scapular kinematics and subacromial space width in vivo." Journal of Biomechanics 2005;38:755-60. doi:10.1016/j.jbiomech.2004.05.020. (6 pages).
Graichen H, Stammberger T. Bonel H, Karl-Hans E, Reiser M, Eckstein F., "Glenohumeral translation during active and passive elevation of the shoulder—a 3D open-MRI study." Journal of Biomechanics 2000;33:609-13.doi:10.1016/S0021-9290(99)00209-2. (5 pages).
Harryman DT, Sidles JA, Harris SL, Lippitt SB, Matsen FA., "The effect of articular conformity and the size of the humeral head component on laxity and motion after glenohumeral arthroplasty." J. Bone Joint Surg Am 1995;77-A:555-63.No doi found. (10 pages).
Huysmans PE, Haen PS, Kidd M, Dhert WJ, Willems JW., "The shape of the inferior part of the glenoid: a cadaveric study." J Shoulder Elbow Surg. 15(6):759-63. doi:10.1016/j.jse.2005.09.001 (5 pages).
Karelse et al., "The Pillars of the Scapula", Clinical Anatomy, 2007, pp. 392-399, vol. 20, Belgium (8 pages).
Erichsen, "Injuries of the Nervous System on Railway and Other Injuries of the Nervous System", The Classic Article in Clinical Orthopaedics and Related Research, Mar. 1997, pp. 47-51, No. 458, Walton and Moberly, London (5 pages).
Iannotti JP, Gabriel JP, Schenck SL, Evans BG, Misra S., "The normal glenohumeral relationships. An anatomical study of one hundred and forty shoulders." J. Bone Joint Surg Am. 1992;74(4); 491-500. No doi found. (11 pages).
Karduna AR, Williams GR, Williams JL, Ianotti JP., "Glenohumeral Joint translations before and after local shoulder arthroplasty." J Bone Joint Surg 1997;79-A, 1166-74. No doi found. (10 pages).
Lee SB, Kim KJ, O'Driscoll SW, Morrey BF, An KN., "Dynamic glenohumeral stability provided by the rotator cuff muscles in the mid-range and end-range of motion." A study in cadavera. J. Bone Joint Surg Am. 2000;82(6):849-57. No doi found (10 pages).
Lewis GS, Bryce CD, Davison AC, Hollenbeak CS, Piazza SJ, Armstrong AD., "Location of the optimized centerline of the glenoid vault: a comparison of two operative techniques with use of three-dimensional computer modeling." J Bone Joint Surg Am, 2010;92:1188-94. doi:10.2106/JBJS.I.00131. (8 pages).
Mahfouz M, Nicholoson G, Komistek R, Hovis D, Kubo M., "In vivo determination of the dynamics of normal, rotator cuff-deficient, total, and reverse replacement shoulders." J Bone Joint Surg Am. 2005;87 Suppl 2:107-13. doi:10.2106/JBJS.E.00483 (8 pages).
Massimini DF, Li G, Warner JP., "Glenohumeral contact kinematics in patients after total shoulder arthroplasty." J Bone Joint Surg Am. Apr. 2010;92(4):916-26. doi:10.2106/JBJS.H.01610. (12 pages).
Matsen FA., "Early effectiveness of shoulder arthroplasty for patients who have primary glenohumeral degenerative joint disease." J Bone and Joint Surg 1996;78-A:260-4. No doi found. (6 pages).
Nyffeler RW, Sheikh R, Atkinson TS, Jacob HA, Favre P, Gerber C., "Effects of glenoid component version on humeral head displacement and joint reaction forces: an experimental study." J Shoulder Elbow Surg. 2006;15:625-9. doi:10.1016/j.jse.2005.09.016. (5 pages).
Nyffeler RW, Werner CM, Sukthankar A, Schmid MR, Gerber C., "Association of a large lateral extension of the acromion with rotator cuff tears." J. Bone Joint Surg Am. 2006;88-800-5. No doi found (7 pages).
Pappas GP, Blemker SS, Beaulieu CF, McAdams TR, Whalen ST, Gold GE., "In vivo anatomy of the Neer and Hawkins sign positions for shoulder impingement." J Shoulder Elbow Surg 2006;15:40-9. doi:10.1016/j.jse.2005.04.007. (10 pages).
Pearl ML, Krurtz S., "Geometric analysis of commonly used prosthetic systems for proximal humeral replacement." J Bone Joint Surg 1999;81-A:660-71. No doi found (13 pages).
Scalise JJ, Codsi MJ, Bryan J, Brems JJ, Iannotti JP., "The influence of three-dimensional computed tomography images of the shoulder in preoperative planning for total shoulder arthroplasty." J Bone Joint Surg Am. 2008;90:2438-45.doi:10.2106/JBJS.G.01341. (9 pages).
Schiffern SC, Rozencwaig R, Antoniou J, Richardson ML, Matsen FA III., "Anteroposterior centering of the humeral head on the glenoid in vivo." Am J Sports Med. 2002;30(3):382-7. No doi found. (7 pages).
Soslowsky LJ, Flatow EL, Bigliani LU, Pawluk RJ, Ateshian GA, Mow VC., "Quantitation of in situ contact areas at the glenohumeral joint: a biomechanical study." J Orthop Res. 1992; 10:524-34. doi:10.1002/jor.1100100407. (11 pages).
Takase K, Yamamoto K, Imakiire A, Burkhead WZ Jr., "The radiographic study in the relationship of the glenohumeral joint." J Orthop Res. 2004;22:298-305. doi:10.1016/50736-0266(03)00187-6 (8 pages).
Tokgoz N, Kanatli U, Voyvoda Nk, Gultekin S, Bolukbasi S, Tali ET., "The relationship of glenoid and humeral version with supraspinatus tendon tears." Skeletal Radion. 2007;36:509-14. No doi found. (6 pages).
Werner CML, Weishaupt D, Blumenthal S, Curt A, Favre P, Gerber C., "Effect of experimental suprascapular nerve block on active glenohumeral translations in vivo." J Orthop Res 2006;24:491-500. doi:10.1002/jor.20011. (10 pages).
Matsen III, Fredereick A., et al., "Shoulder Arthroplasty: The Socket Perspective," Journal of Shoulder and Elbow Surgery, Oct. 2007; 1: 24S-247S (7 pages).
Extended European Search Report corresponding to European Application No. 12760274.6, dated Jun. 27, 2014 (6 pages).
Piasecki et al., Review Article: "Glenoid Bone Deficiency in Recurrent Anterior Shoulder Instability: Diagnosis and Management," JAm Acad. Ortho. Surg. 2009, vol. 17, pp. 482-493.
Extended European Search Report corresponding to European Patent Application No. 12760199.5, dated Aug. 7, 2014 (6 pages).
Extended European Search Report corresponding to European Patent Application 12760666.3, dated May 13, 2014 (10 pages).

* cited by examiner

DEVICE AND METHOD FOR RETROVERSION CORRECTION FOR SHOULDER ARTHROPLASTY

CROSS-REFERENCE TO RELATED APPLICATIONS

This application is related to U.S. patent application Ser. No. 13/051,011, entitled "Circular Glenoid Method for Shoulder Arthroscopy", which was filed on Mar. 18, 2011 (now U.S. Pat. No. 8,764,836, issued on Jul. 1, 2014), U.S. patent application Ser. No. 13/051,026, entitled "Combination Reamer/Drill Bit for Shoulder Arthroscopy", which was also filed on Mar. 18, 2011, and U.S. patent application Ser. No. 13/051,062, entitled "Revision Glenoid Device and Method", which was also filed on Mar. 18, 2011 (now U.S. Pat. No. 8,551,177, issued on Oct. 8, 2013), the contents of which are each incorporated herein by reference.

TECHNICAL FIELD OF THE INVENTION

The present invention relates generally to the field of orthopedics, and, more particularly, to glenoid component apparatuses for shoulder arthroplasty and methods for using them.

BACKGROUND

Figure 1:
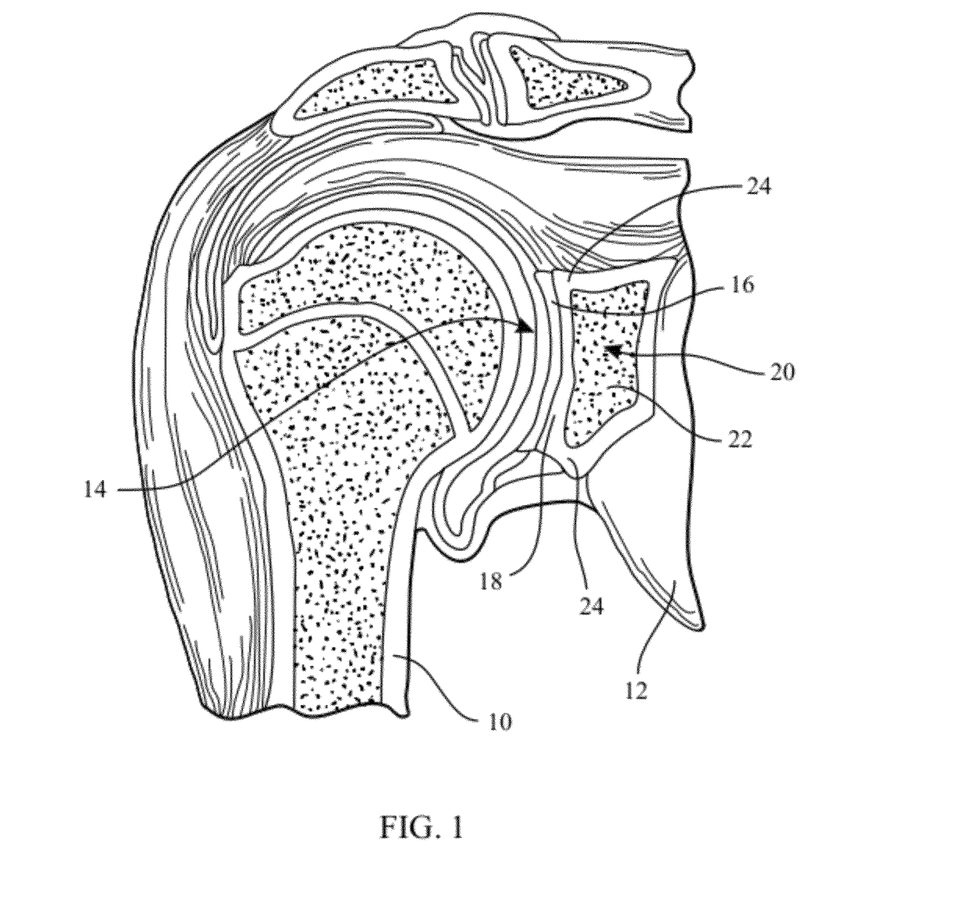
FIG. 1 depicts a coronal view of an anatomically normal shoulder joint.

As depicted in FIG. 1, a typical shoulder or glenohumeral joint is formed in a human body where the humerus 10 movably contacts the scapula 12. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 24 at a periphery of the glenoid vault 20 that is attached to the cartilage 16. During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed. Arthroplasty is the surgical replacement of one or more bone structures of a joint with one or more prostheses.

Shoulder arthroplasty often involves replacement of the glenoid fossa of the scapula with a prosthetic glenoid component. The conventional glenoid component typically provides a generally laterally or outwardly facing generally concave bearing surface against which a prosthetic humeral head (or, alternatively, the spared natural humeral head in the case of a glenoid hemi-arthroplasty) may bear during operation of the joint. The conventional glenoid component typically also includes a generally medially or inwardly projecting stem for fixing the glenoid component in a cavity constructed by suitably resecting the glenoid fossa 14 and suitably resecting cancellous bone 22 from the glenoid vault 20.

The goal of shoulder arthroplasty is to restore normal kinematics to the shoulder. Accordingly, known systems attempt to replicate the normal kinematics by carefully controlling the geometry of the articulating surfaces in the joint as well as the positioning of the prostheses in the bones in which the prostheses are implanted. Thus, the articulating surface of a humeral component is typically spherical and positioning of the humeral component is accomplished by using the anatomical neck of the humerus as the reference plane for reconstruction of the humeral head.

Figure 2:
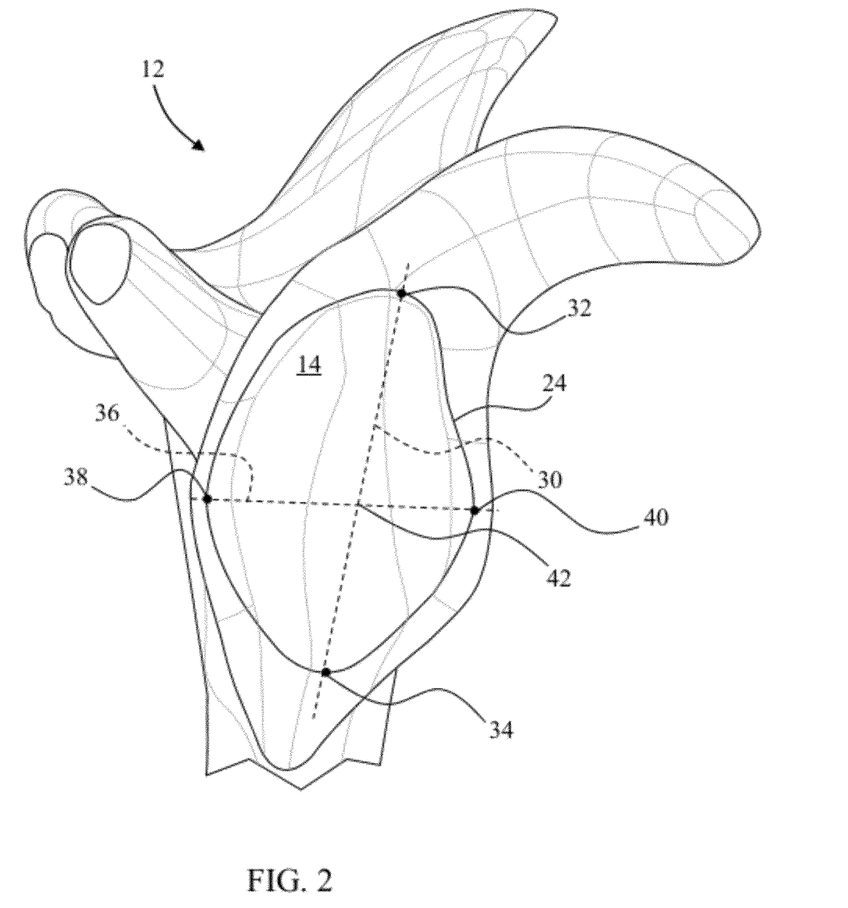
FIG. 2 depicts a sagittal view of the shoulder joint of FIG. 1.

In known systems, the glenoid component is positioned in the geometric center of the glenoid fossa. The geometric center is established by generating a line from the most superior point of the glenoid rim to the most inferior point of the glenoid rim ("Saller's line"). A second line is generated between the most posterior point of the glenoid rim and the most anterior point of the glenoid rim. The intersection of the two generated lines is considered to be the geometric center of the area circumscribed by the glenoid rim. By way of example, FIG. 2 depicts a sagittal view of the scapula 12. In FIG. 2, Saller's line 30 extends between the most superior point 32 of the glenoid rim 24 and the most inferior point 34 of the glenoid rim 24. A second line 36 extends from the most posterior point 38 of the glenoid rim 24 and the most anterior point 40 of the glenoid rim. The geometric center 42 of the glenoid fossa 14 is located at the intersection of the line 36 and Saller's line 30. As used herein, the terms anterior, posterior, superior, and inferior, unless otherwise specifically described, are used with respect to the orientation of the scapula 12 as depicted in FIG. 2.

Depending upon the particular morphology of an individual, preparing a glenoid to receive an implant once the desired location for the implant is determined can be problematic. One particularly difficult morphology is referred to as "glenoid retroversion." In glenoid retroversion, the glenoid fossa has experienced uneven deterioration. Since known glenoid components are configured to be implanted upon a level base of bone, significant surface preparation is required before the glenoid component can be implanted. In some approaches, a bone graft is used to even out the glenoid fossa so that a desired orientation of a glenoid implant can be achieved. Using a bone grafting procedure, however, is typically a two-stage procedure which complicates the implant procedure.

In another approach, the area of the glenoid fossa in which the implant is to be implanted is simply planarized to the level of the deepest defect and a thicker glenoid implant is used to achieve the desired position for the articulating surface of the glenoid component. While effective, this approach necessitates removal of a large amount of bone.

There remains a need for a glenoid component that allows for establishing normal kinematics. There is a further need for a technique, instrumentation, and implant that facilitates positioning of such a component. A glenoid component that can be positioned in a manner that reduces the amount of bone that is required to be removed without overly complicating the implant procedure is also needed.

SUMMARY OF THE INVENTION

The present invention in one embodiment provides a kit for implanting a glenoid component including a retroversion glenoid component with a generally flat glenoid bone contacting surface defining a first plane, a first offset peg extending away from the glenoid bone contacting surface, a concave articulating surface, an upper surface extending about the concave articulating surface and generally opposite to the glenoid bone contacting surface, the upper surface defining a second plane, the second plane angled with respect to the first plane, and a drill guide configured to guide a drill in forming a bore in a scapula to receive the first offset peg.

In another embodiment, a kit for implanting a glenoid component includes a retroversion glenoid component including a generally flat glenoid bone contacting surface defining a first plane, a glenoid peg extending away from the glenoid bone contacting surface and defining a glenoid peg axis, the glenoid peg axis forming an angle other than 90 degrees with the first plane, and a concave articulating surface, and a drill guide configured to guide a drill in forming a bore in a scapula, the drill guide including a generally flat drill guide bone contacting surface defining a second plane and a drill guide peg extending away from a bottom portion of the drill guide and defining a drill guide peg axis, the drill guide peg axis forming an angle other than 90 degrees with the second plane, wherein a first minimum angle defined by the center peg axis and the first plane is the same as a second minimum angle defined by the drill guide peg axis and the second plane.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

DETAILED DESCRIPTION

Like reference numerals refer to like parts throughout the following description and the accompanying drawings.

Figures 3, 4, 5:
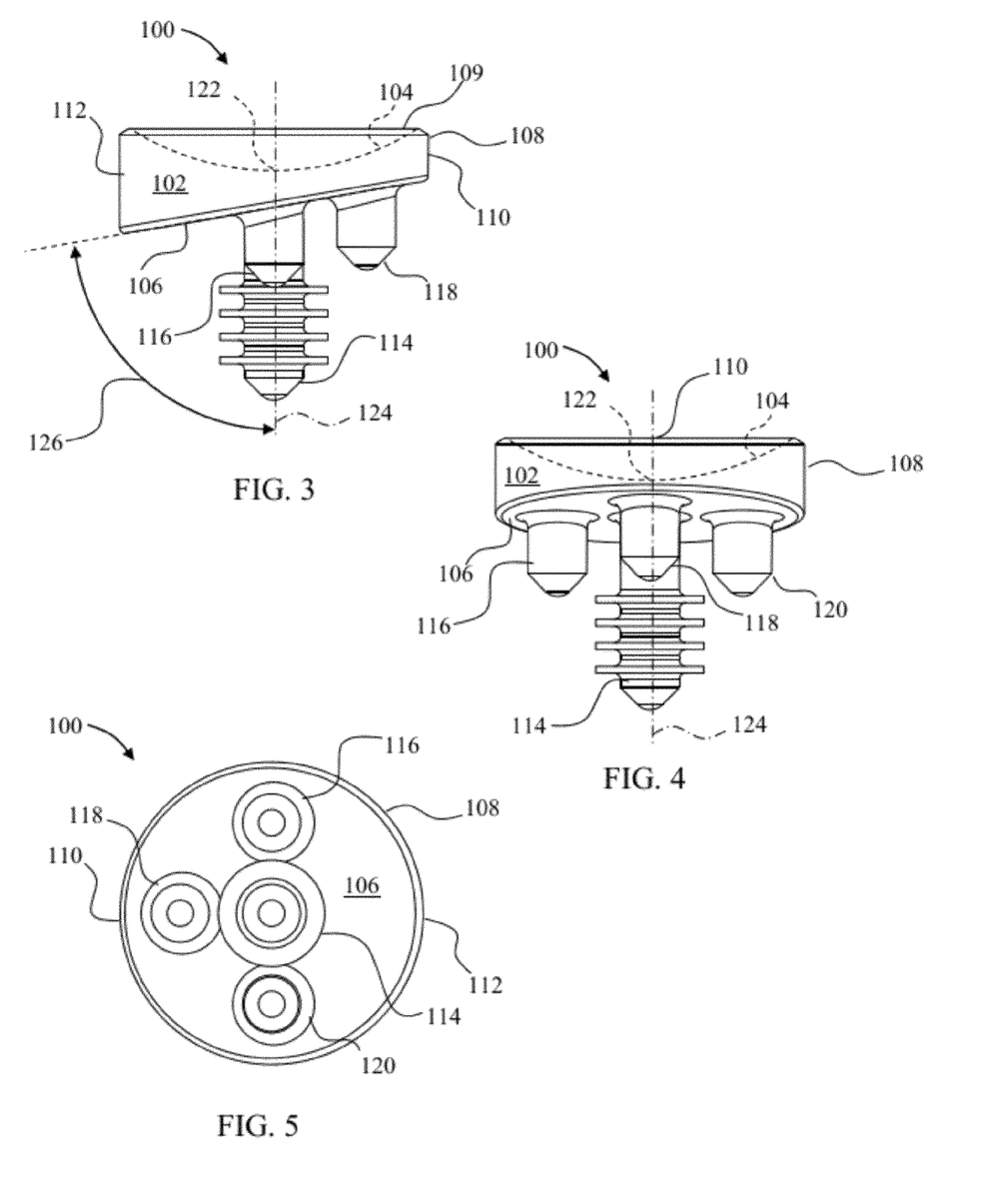
FIG. 3 depicts a side plan view of a retroversion glenoid component that may be implanted in a scapula in accordance with principles of the invention.
FIG. 4 depicts a plan view of the retroversion glenoid component of FIG. 3 centered on the minimum height area of the retroversion glenoid component.
FIG. 5 depicts a bottom plan view of the retroversion glenoid component of FIG. 3.

FIGS. 3-5 depict a retroversion glenoid component 100. The glenoid component 100 includes a body portion 102 including a spherical articulating surface 104 and an opposite bone contacting surface 106. The bone contacting surface 106 is generally planar. An outer wall 108 extends away from the bone contacting surface 106 and defines an outer periphery of the body portion 102 that is circular. The body portion 102 is generally wedge shaped when viewed from the side since the upper end 109 of the glenoid component 100 defines a plane that is angled with respect to the angle of the bone contacting surface 106 as seen most clearly in FIG. 3. Thus, the height of the outer wall 108 from the bone contacting surface to the upper end of the glenoid component 100 ranges from a minimum height area 110 to a maximum height area 112 which is directly opposite to the minimum height area 110.

The glenoid component 100 further includes a finned center peg 114 that extends away from the center of the bone contacting surface 106. Three offset pegs 116, 118, and 120 extend away from the bone contacting surface 106 at locations between the center peg 114 and the outer wall 108. The offset peg 118 is aligned with the center peg 114 and the minimum height area 110 while the offset pegs 116 and 120 are at angular locations about the bone contacting surface 106 halfway between the minimum height area 110 and the maximum height area 112 (see FIG. 5). The nadir 122 of the spherical articulating surface 104 is located on the centerline 124 of the glenoid component 100.

Additionally, the finned center peg 114 defines a longitudinal axis that in this embodiment is the same as the centerline 124. Each of the three offset pegs 116, 118, and 120 define longitudinal axes (not shown) that are parallel to the centerline 124. The longitudinal axis 124 is not perpendicular to the plane defined by the bone contacting surface 106. Thus, the centerline 124 and the bone contacting surface 106 define a minimum angle 126 in the plane of FIG. 3.

The glenoid component 100 in this embodiment is an integrally formed unit made from a durable biocompatible plastic or any other suitable durable biocompatible material. For example, the glenoid component 100 may be made from a polyethylene. One particular polyethylene that is well suited for glenoid component 100 is a high molecular weight polyethylene, for example ultra-high molecular weight polyethylene ("UHMWPE"). One such UHMWPE is sold as by Johnson & Johnson of New Brunswick, N.J. as MARATHON™ UHMWPE and is more fully described in U.S. Pat. Nos. 6,228,900 and 6,281,264 to McKellop, which are incorporated herein by reference.

In embodiments wherein the articulating surface 104 and the other portions of the glenoid component 100 are made from different materials, the portions of the glenoid component 100 other than the articulating surface 104 may be made from a suitable biocompatible metal such as, for example, a cobalt chromium alloy, a stainless steel alloy, a titanium alloy, or any other suitable durable material. In these embodiments, the articulating surface 104 is secured to the body portion 102 in any suitable manner. For example, articulating surface 104 may be bonded to body portion 102, or articulating surface 104 could be made from polyethylene and compression molded to body portion 102. Alternately, the articulating surface 104 may be glued to the body portion 102 by, for example, an adhesive. Alternatively, articulating surface 104 may be mechanically interlocked to the body portion 102 by taper locking or otherwise press-fitting the articulating surface 104 into the body 102 and the body 102 may include any other suitable interlocking features, for example, rib(s), lip(s), detent(s), and/or other protrusion(s) and mating groove(s), channel(s), or indent(s) (not shown).

In alternative embodiments, one or more of the outer wall 108, the bone contacting surface 106, the center peg 114 and the offset pegs 116, 118, and 120 may include a porous coating to facilitate bone in-growth into the glenoid component 100. The porous coating may be any suitable porous coating and may for example be POROCOAT®, a product of Johnson & Johnson of New Brunswick, N.J. and more fully described in U.S. Pat. No. 3,855,638 to Pilliar, which is incorporated herein by reference.

Figures 6, 7, 8, 9:
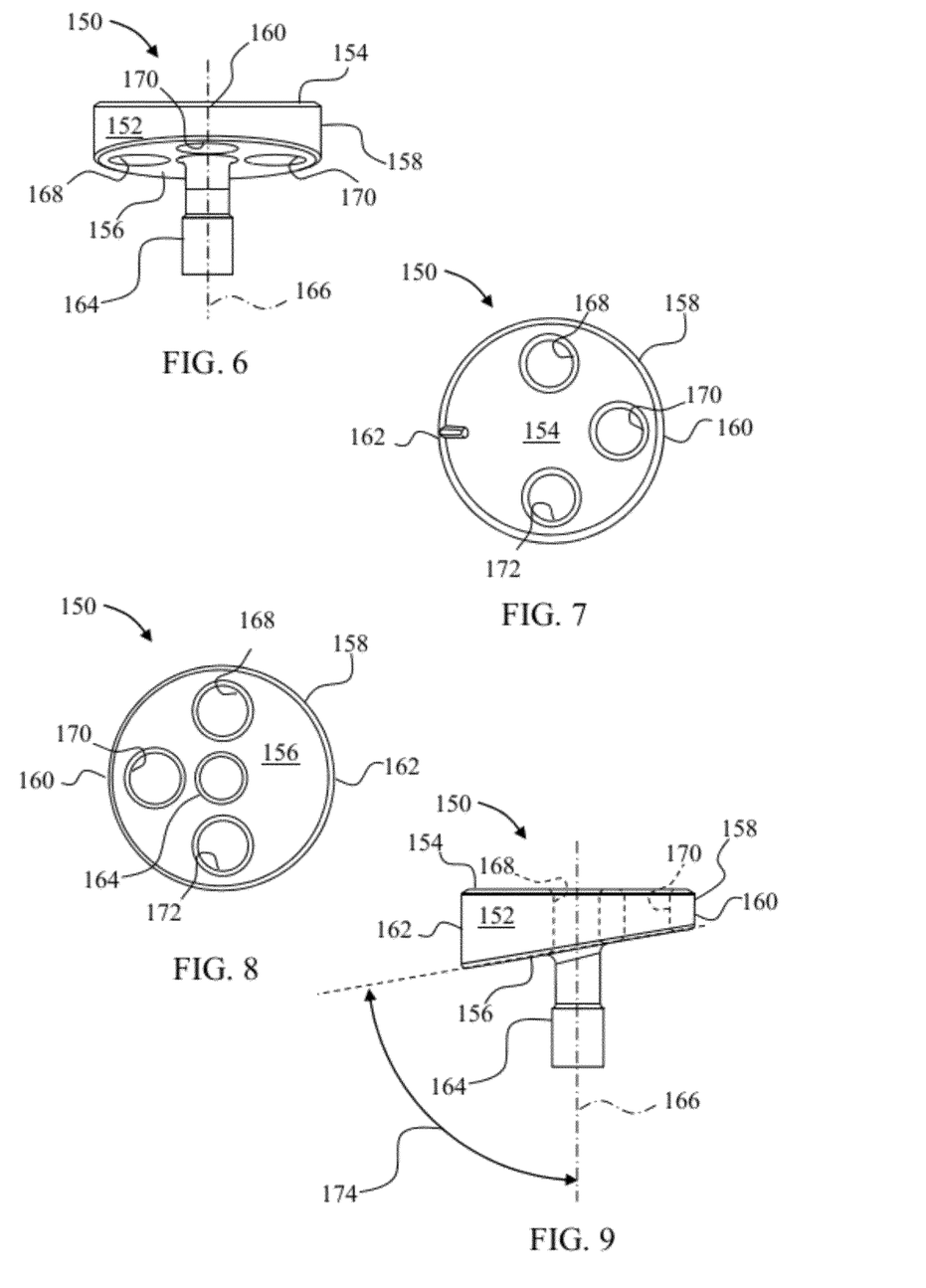
FIG. 6 depicts a plan view of a drill guide that may be included in a kit along with the retroversion glenoid component of FIG. 3, the drill guide having a bottom surface that is angled with respect to a center peg in the same way that the bone contacting surface of the retroversion glenoid component of FIG. 3 is angled with respect to the finned center peg of FIG. 3, and with guide holes that correspond to the offset pegs of the retroversion glenoid component of FIG. 3 centered on the minimum height area of the drill guide.
FIG. 7 depicts a top plan view of the drill guide of FIG. 6.
FIG. 8 depicts a bottom plan view of the drill guide of FIG. 6.
FIG. 9 depicts a side plan view of the drill guide of FIG. 6, which side view corresponds to the side view of the retroversion glenoid component in FIG. 3.

The glenoid component 100 may be included in a kit incorporating instrumentation that may be used to facilitate implantation of the glenoid component 100. One item that may be included in the kit is a drill guide 150 depicted in FIGS. 6-9. The drill guide 150 includes a body portion 152 including an upper surface 154 and an opposite bone contacting surface 156. The shape of the body portion 152 is substantially the same as the body portion 102. Thus, the bone contacting surface 156 is generally planar. An outer wall 158 extends away from the bone contacting surface 156 and defines an outer periphery of the body portion 152. The body portion 152 is generally wedge shaped as seen most clearly in FIG. 9. Thus, the height of the outer wall 158 from the bone contacting surface 156 to the upper surface 154 of the drill guide 150 ranges from a minimum height area 160 to a maximum height area 162.

The drill guide 150 further includes a center peg 164 that extends away from the center of the bone contacting surface 156. The center peg 164 is about the same width as the finned center peg 114 of the glenoid component 100, and slightly shorter than the finned center peg 114. The center peg 164 defines a center axis 166. Three offset guide holes 168, 170, and 172 extend between the bone contacting surface 156 and the upper surface 154 at locations between the center peg 164 and the outer wall 158. Each of the three guide holes 168, 170, and 172 define longitudinal axes (not shown) that are parallel to the center axis 166.

For purposes that are described more fully below, each of the three guide holes 168, 170, and 172 corresponds to a respective one of the three offset pegs 116, 118, and 120. Thus, the radial spacing of the guide holes 168, 170, and 172 from the center peg 164 is the same as the radial spacing of the respective offset peg 116, 118, or 120 from the center peg 114. Moreover, the angular position of the guide holes 168, 170, and 172 about the bone contacting surface 156 with respect to the minimum height area 160 is the same as the angular position of the respective offset peg 116, 118, or 120 about the bone contacting surface 106 with respect to the minimum height area 110. In other words, the guide hole 170 is at zero degrees (see FIG. 8) while the hole 172 is at 90 degrees, and the offset peg 118 is at zero degrees (see FIG. 5) and the offset peg 120 is at 90 degrees.

Figure 10:
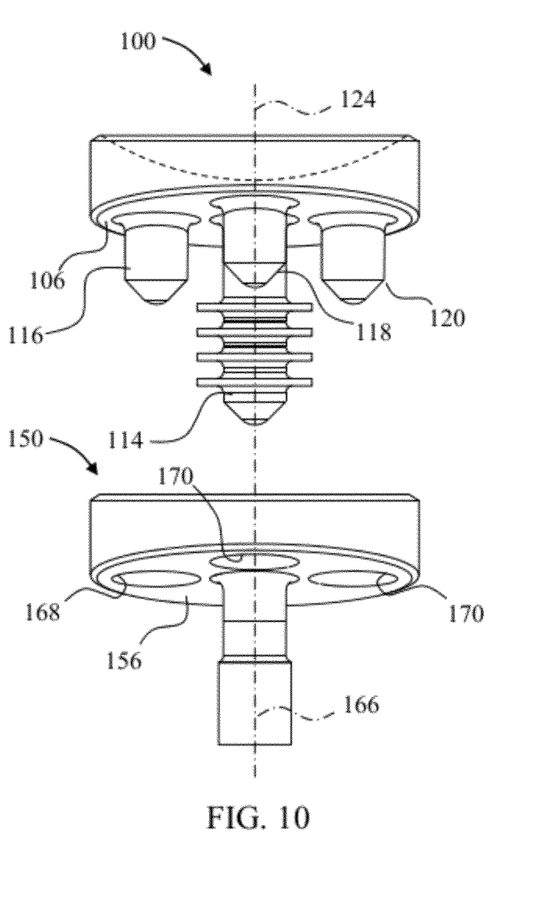
FIG. 10 depicts a plan view of the retroversion glenoid component of FIG. 3 centered on the minimum height area of the retroversion glenoid component and positioned above the drill guide of FIG. 6 centered on the minimum height area of the drill guide to show correspondence between the guide holes of the drill guide and the offset pegs of the retroversion glenoid component as well as the correspondence between the location of the finned peg of the retroversion glenoid component and the peg of the drill guide.
Figure 11:
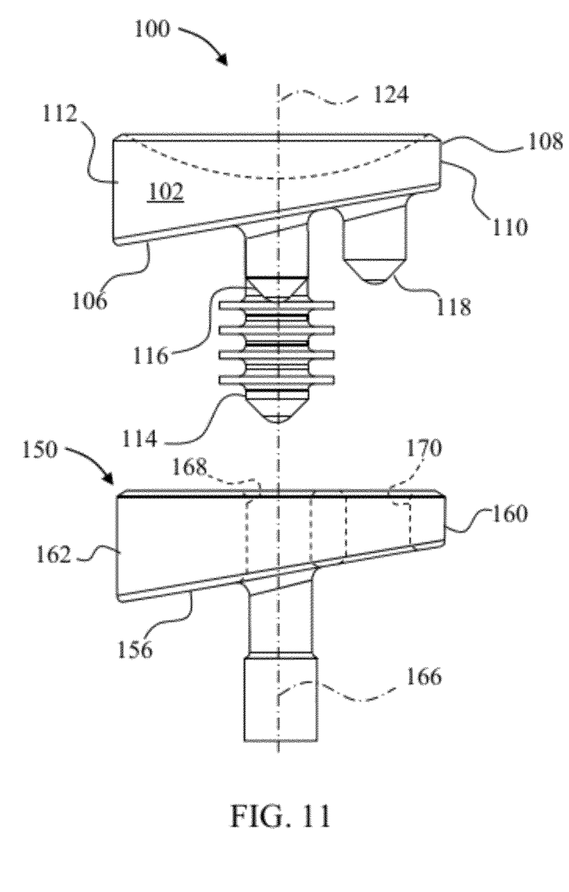
FIG. 11 depicts a side plan view of the retroversion glenoid component of FIG. 3 positioned above the drill guide of FIG. 6 to show correspondence between the guide holes of the drill guide and the offset pegs of the retroversion glenoid component as well as the correspondence between the location of the finned peg and the angle formed with the bone contacting surface of the retroversion glenoid component and the center peg and the angle formed with the bone contacting surface of the drill guide.

Additionally, the center axis 166 is not perpendicular to the plane defined by the bone contacting surface 156. Thus, the center axis 166 and the bone contacting surface 156 define a minimum angle 174 in the plane of FIG. 9. The minimum angle 174 is identical to the minimum angle 126 of the retroversion glenoid component 100. Thus, when the center line is 124 aligned with the center axis 166 as depicted in FIGS. 10-11, the longitudinal axis of each of the guide holes 168, 170, and 172 will be aligned with the longitudinal axis of the respective offset peg 116, 118, or 120 and the bone contacting surface 106 lies in a plane parallel to the plane defined by the bone contacting surface 156. By way of example, in FIGS. 10-11, the guide hole 170 corresponds with the offset peg 118, and the longitudinal axes of the guide hole 170 and the offset peg 118 is coextensive with the axis 174.

Figure 12:
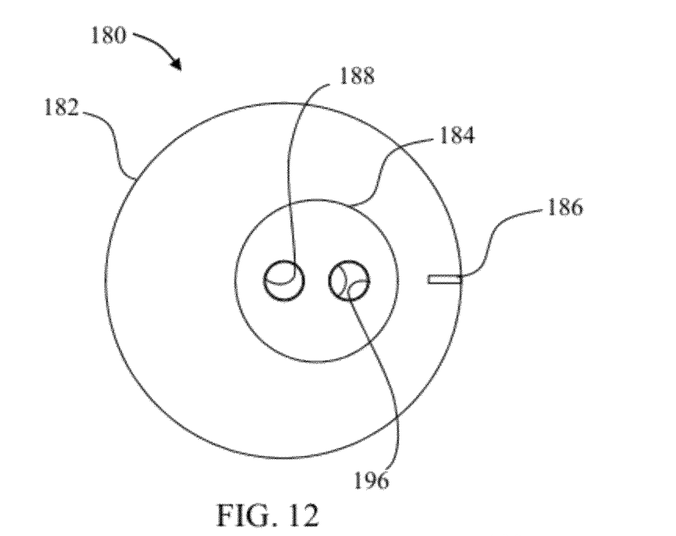
FIG. 12 depicts a top plan view of a pin placement guide that can be included in a kit along with the retroversion glenoid component of FIG. 3 and the drill guide of FIG. 6.
Figure 13:
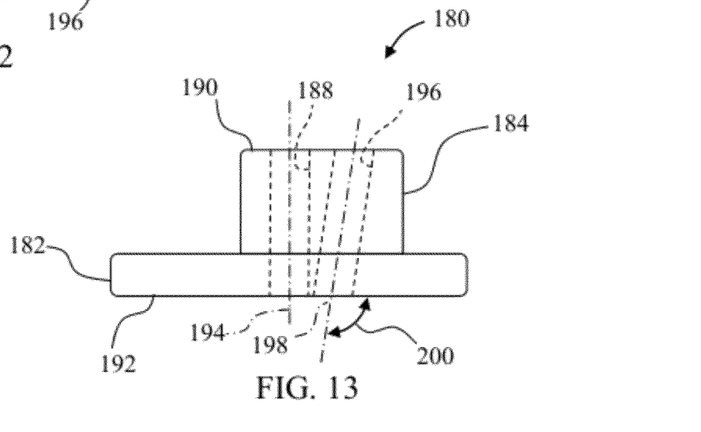
FIG. 13 depicts a side plan view of the pin placement guide of FIG. 12 showing one pin guide hole that is perpendicular to the bottom surface of the pin placement guide and a second pin guide hole that defines a longitudinal axis that forms an angle with the bone contacting surface of the pin placement guide that is the same as the angle formed by the finned peg and the bone contacting surface of the retroversion glenoid component and the angle formed by the center peg and the bone contacting surface of the drill guide as the retroversion glenoid component and the drill guide are viewed from the side as in FIG. 11.

A kit including the glenoid component 100 may further include a pin placement guide 180 shown in FIGS. 12 and 13. The placement guide 180 includes a base portion 182 and an elevated portion 184. A reference mark 186 is provided on the base portion 182. A first guide hole 188 extends from the upper surface 190 of the elevated portion 184 to the bottom surface 192 of the base portion 182. The first guide hole 188 defines a central axis 194 that is perpendicular to the bottom surface 192. A second guide hole 196 also extends from the upper surface 190 of the elevated portion 184 to the bottom surface 192 of the base portion 182. The second guide hole 196 defines a central axis 198. The central axis 198 forms an angle 200 with the bottom surface 192 that is identical to the angle formed between the center line 124 of the glenoid component 100 and the bone contacting surface 106 of the glenoid component 100 in the plane of the side plan view of FIG. 3.

Figure 14:
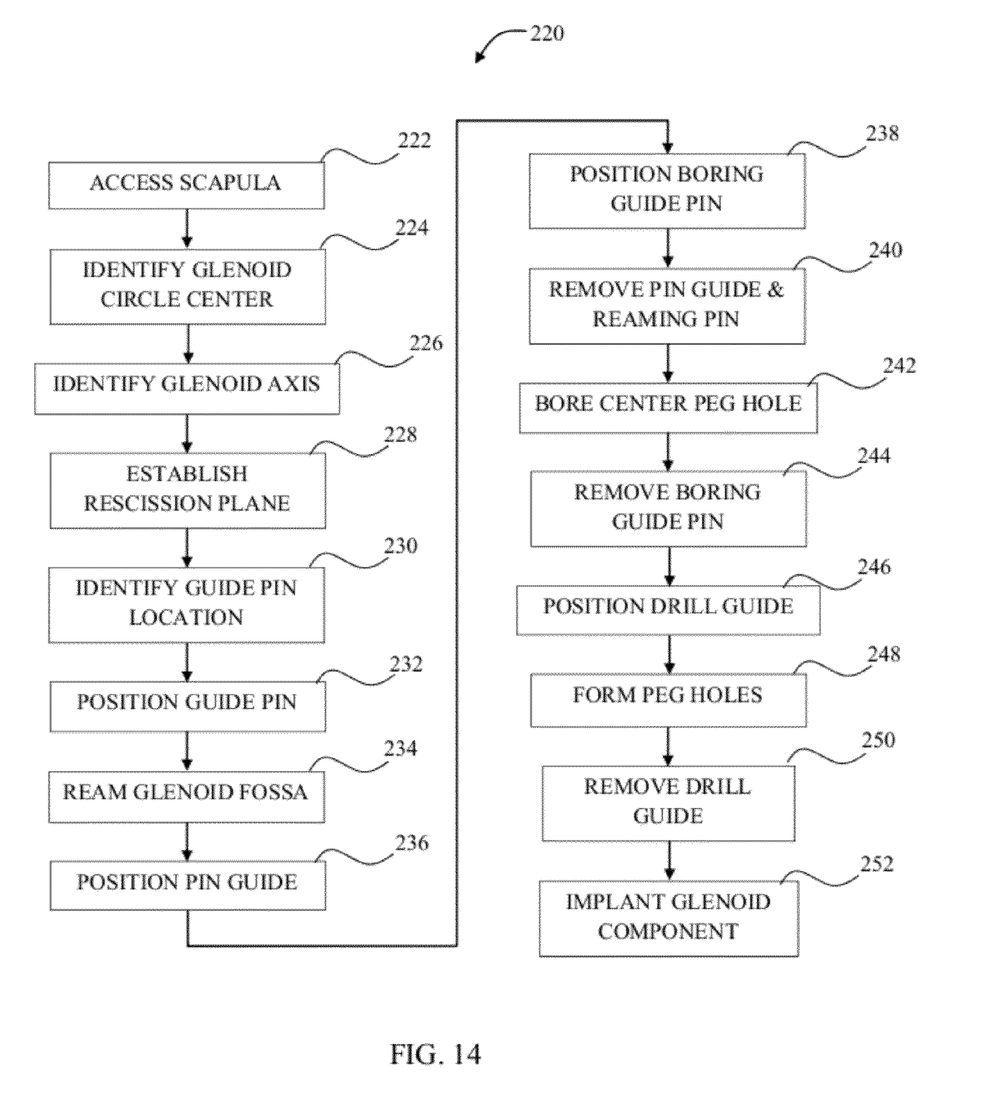
FIG. 14 depicts a medical procedure that may be used to implant the retroversion glenoid component of FIG. 3 into a scapula using a kit that includes a corresponding drill guide of FIG. 6 and pin placement guide of FIG. 12.

A kit including the glenoid component 100 may be implanted into the scapula 12 in accordance with a procedure 220 depicted in FIG. 14. In accordance with the procedure 220, a scapula 12 is accessed at block 222 in accordance with a desired surgical approach. At block 224, the center of an inferior glenoid circle, further described in co-pending U.S. patent application Ser. No. 13/051,011, is identified for the scapula. While visual identification of the inferior glenoid circle and hence the center of the inferior glenoid circle is possible once the scapula 12 is accessed at block 222, the center of the inferior glenoid circle may alternatively be identified prior to or after incising a patient with the aid of imaging or other techniques.

Once the center of the inferior glenoid circle is identified at block 224, a glenoid axis which extends through the center of the inferior glenoid circle and is perpendicular to the articulating surface of the glenoid is identified (block 226). In alternative approaches, the glenoid axis may extend through the scapula at locations other than the center of the inferior glenoid circle. The glenoid axis may be identified prior to or after incising a patient with the aid of imaging or other techniques.

Next, a rescission plane is determined for the glenoid (block 228). The "rescission plane" as that term is used herein is a plane to which the glenoid can be excised which results in a substantially continuous extent of bone suitable for placement of the glenoid component 100 while minimizing the amount of bone required to be excised. At block 230, the desired reaming guide pin location is identified. The placement of the reaming guide pin is selected to be perpendicular to the rescission plane and at a location in the glenoid whereat once the pin placement guide 180 is positioned with the reaming guide pin extending through the first guide hole 188 of the pin placement guide 180, as discussed more fully below, the central axis 198 of the second guide hole is coextensive with the glenoid axis. The analysis of blocks 228 and 230 may be identified prior to or after incising a patient with the aid of imaging or other techniques.

At block 232, the reaming guide pin is positioned at the identified position and the glenoid is reamed at block 234 to the identified rescission plane using the reaming guide pin to guide a reamer. Once the identified rescission plane has been exposed, the reamer is removed and at block 236 the pin placement guide 180 is positioned on the rescission plane with the reaming guide pin extending through the first guide hole 188. The pin placement guide 180 is rotated as necessary to align the central axis 198 of the second guide hole 196 with the glenoid axis. If desired, the reference mark 186 may be used to assist in positioning of the pin placement guide 180. Precision of the foregoing steps may be increased using computer assisted procedures.

Once the pin placement guide 180 is positioned on the rescission plane, a boring guide pin is inserted into the scapula 12 through the second guide hole 196 (block 238). The pin placement guide 180 and the reaming guide pin are then removed (block 240). At block 242 a center peg hole is bored using the boring guide pin as a guide and at block 244 the boring guide pin is removed.

The drill guide 150 is then positioned on the reamed glenoid by positioning the center peg 164 in the center peg hole (block 246). Because the center axis 166 forms an angle with the bone contacting surface 156 that is identical to the angle formed by the centerline 124 of the glenoid component 100 and the bone contacting surface 106 of the glenoid component 100, and because the angle between the central axis 198 of the second guide hole and the bottom surface 192 of the placement guide 180 is identical to the angle formed by the centerline 124 of the glenoid component 100 and the bone contacting surface 106 of the glenoid component 100, the bone contacting surface 156 of the drill guide 150 will lie flat upon the resected glenoid at only a single position. Once the drill guide 150 is positioned flatly upon the resected glenoid, the guide holes 168, 170, and 172 are used to guide formation of peg holes in the glenoid (block 248).

The drill guide 150 is then removed (block 250). At block 252, the glenoid component 100 is positioned on the resected glenoid by insertion of the center peg 114 into the center peg hole and substantially simultaneous insertion of the offset pegs 116, 118, and 120 into the peg holes. As with the drill guide 150, the glenoid component 100 may only be installed at a single orientation because the set pegs 116, 118, and 120 are not symmetrically located about the bone contacting surface 106. Once positioned, the centerline 124 of the glenoid component 100 is coextensive with the glenoid axis and the nadir 122 is positioned at the center of the lower glenoid circle.

Figure 15:
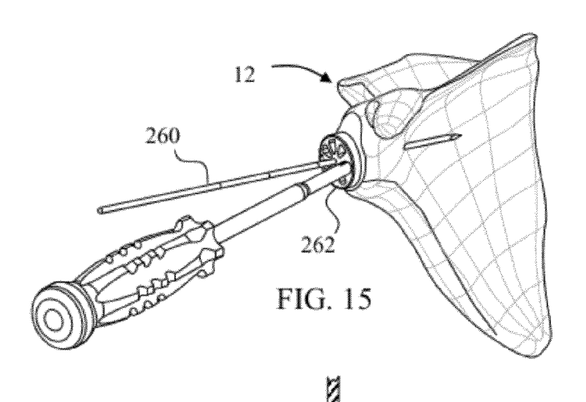
FIG. 15 depicts a perspective view of the reaming guide pin placed into the scapula of FIG. 1 in accordance with principles of the medical procedure of FIG. 14.
Figures 16, 17, 19:
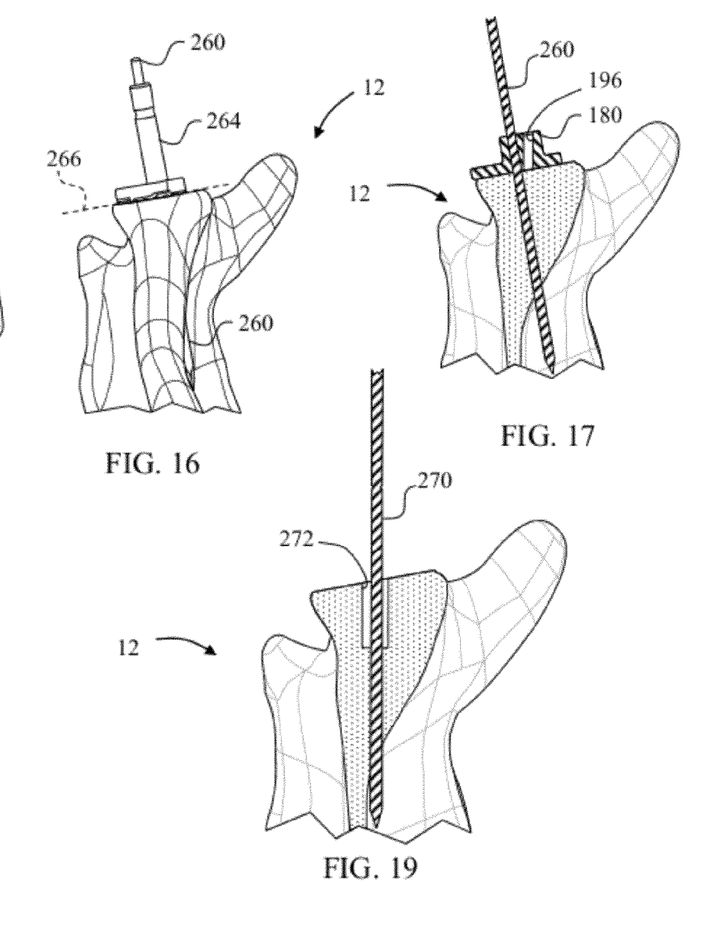
FIG. 16 depicts a side plan view of the reaming guide pin of FIG. 15 used to guide reaming of the scapula of FIG. 1, which is depicted at an angle looking upwardly at the scapula, to a rescission plane in accordance with principles of the medical procedure of FIG. 14.
FIG. 17 depicts a cross sectional view of the pin placement guide of FIG. 12 mounted on the scapula and reaming guide pin of FIG. 16.
FIG. 19 depicts a cross sectional view of the scapula of FIG. 16 after the boring guide pin has been used to bore a peg hole which is angled with respect to the rescission plane in accordance with principles of the medical procedure of FIG. 14.

FIGS. 15-23 depict the scapula 12 at various points of the procedure 220. In FIG. 15, the scapula 12 is depicted after block 232 with a reaming guide pin 260 that has been implanted in the scapula with the assistance of a pin placement guide assembly 262. The reaming guide pin 260 defines a longitudinal axis (not shown) that is offset from the glenoid axis identified at block 226. In FIG. 16, the reaming guide pin 260 has been used to guide a reamer 264 to expose the rescission plane 266. In this example, the exposed plane extends to the lower edge of the glenoid fossa. Because of the angle of the rescission plane 266 with respect to the scapula 12, the peak ridge between the two concave surfaces of the bi-cave glenoid is not removed.

FIG. 17 depicts the scapula 12 once the reamer 264 has been removed and the pin placement guide 180 has been positioned. With the reaming guide pin 260 inserted through the first guide hole 188, full insertion of a boring guide pin 270 (see FIG. 18) may not be possible. In such a situation, the boring guide pin 270 may be partially inserted into the scapula, and then the reaming guide pin 260 removed to allow for full insertion of the boring guide pin 270 into the scapula 12 (see FIG. 18) at 238. In some situations, the reaming guide pin 260 may be fully or partially removed prior to any insertion of the boring guide pin 270 into the scapula 12.

Figure 18:
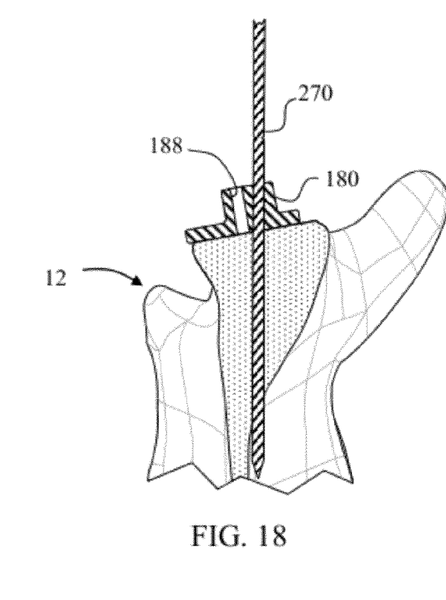
FIG. 18 depicts a cross sectional view the pin placement guide of FIG. 12 used to guide positioning of a boring guide pin in the scapula of FIG. 16 such that the axis defined by the boring guide pin is aligned with the center axis of the finally implanted retroversion glenoid component in accordance with principles of the medical procedure of FIG. 14.

Once the boring guide pin 270 has been fully inserted in the scapula 12 and the reaming guide pin 260 has been removed as depicted in FIG. 18, the longitudinal axis (not shown) of the boring guide pin 270 is coextensive with the glenoid axis (not shown). The pin placement guide 180 may then be removed (block 240). Next, the boring guide pin 270 is used to guide a drill (not shown) to bore a center peg hole 272 (block 242). The boring guide pin 270 is then removed (block 244).

Figures 20, 21, 22, 23:
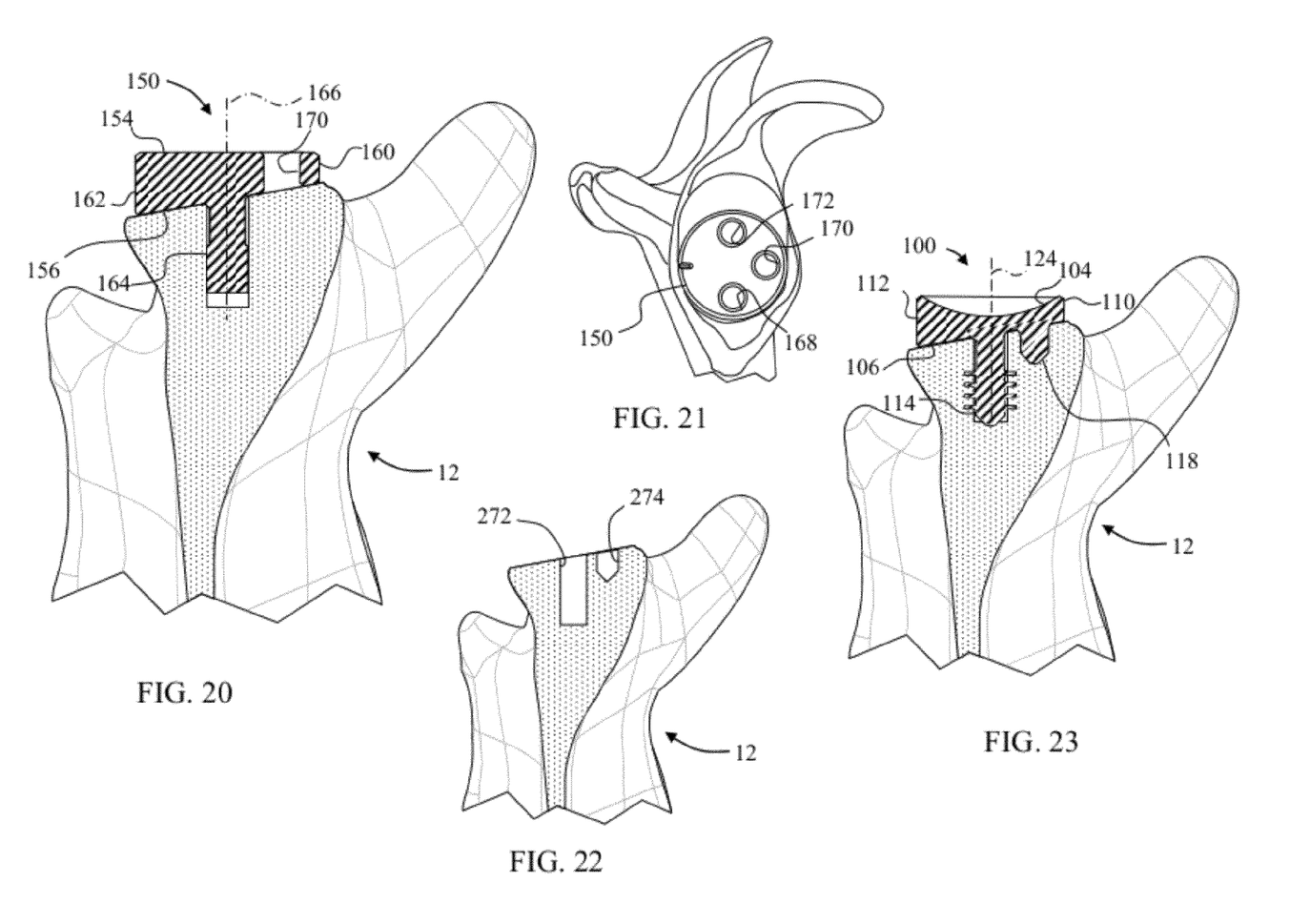
FIG. 20 depicts a cross sectional view of the drill guide of FIG. 6 mounted on the scapula of FIG. 19 with the center peg of the drill guide positioned in the peg hole and the bone contacting surface of the drill guide lying flat upon the reamed portion of the scapula.
FIG. 21 depicts a sagittal view of the scapula of FIG. 20 with the drill guide positioned on the reamed portion of the scapula.
FIG. 22 depicts a cross sectional view of the scapula of FIG. 20 after peg holes have been bored using the drill guide of FIG. 6.
FIG. 23 depicts a cross sectional view of the scapula of FIG. 22 after the retroversion glenoid component of FIG. 3 has been implanted.

With the center peg hole 272 prepared and the boring guide pin 270 removed, the drill guide 150 may be installed onto the scapula 12 (block 246) as shown in FIGS. 20 and 21. As discussed above, because the center axis 166 of the center peg 164 is angled with respect to the bottom surface 156, the bottom surface 1556 will lie flat on the reamed glenoid fossa of the scapula 12 at only one position (see FIG. 20). Moreover, the guide holes 168, 170, and 172 are necessarily positioned over portions of the scapula 12 where a lesser amount of bone has been removed.

With the drill guide 150 installed, the drill guide 150 may be used to guide boring of peg holes to receive the offset pegs 116, 118, and 120 (block 248) resulting on the configuration of FIG. 22 which shows a peg hole 274 spaced apart from the peg hole 272. The glenoid component 100 is then implanted by insertion of the center peg 114 into the peg hole 272, insertion of the offset peg 118 into the peg hole 274, and insertion of the offset pegs 116 and 120 into respective peg holes (not shown). The final implanted configuration is shown in FIG. 23. In FIG. 23, the bone contacting surface 106 is seated on the reamed scapula 12 and the centerline 124 is coextensive with the glenoid axis.

While the foregoing examples detailed only a single glenoid component 100, a kit may incorporate a number of different glenoid components. Each glenoid component in the kit may be of a different diameter. Additionally, glenoid components which have various maximum wall heights and various minimum wall heights so as to exhibit different angles between the bone contacting surface and the center axis of the center peg may be included. In such a kit, multiple drill guides, and pin placement guides may be provided so that the procedure 220 may be performed with the respective glenoid components.

Provision of glenoid components with different wedge shapes as described above allow a surgeon to minimize the amount of bone which must be removed during a retroversion surgical procedure. Additionally, while each of the offset pegs 116, 118, and 120 where shown as having substantially identical shapes and dimensions, in other embodiments that offset pegs may be differently shaped and sized.

Additionally, the procedure 220 may be modified in a number of ways. By way of example, while in the above example the glenoid component 100 was implanted with the nadir 122 aligned with the inferior glenoid circle center at block 252, the nadir 122 may alternatively be offset from the inferior glenoid circle center. For example, the nadir 122 may be offset from the inferior glenoid circle center by about 1.1 mm in a direction superiorly and posteriorly from the inferior glenoid circle center. Imaging and computer based systems may be used to assist in the positioning of the glenoid component at this location.

Moreover, while a specific sequence was described in the procedure 220, many of the steps may be performed in a different order and/or simultaneously with other of the steps.

In accordance with the methods described above, a glenoid component with a spherical articulating surface is implanted at or very near to the spinning point of a shoulder. Because of the location of the glenoid component, a humeral component with a radius of curvature matched to the radius of curvature of the articulating surface may be used to provide a constrained fit. As used herein, the term "matched" means a difference in the radii of curvature of the articulating surfaces of less than 2 mm.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A kit for implanting a glenoid component comprising:
a retroversion glenoid component including a generally flat and circular glenoid bone contacting surface defining a first plane, a first offset peg extending away from the glenoid bone contacting surface, a concave articulating surface, an upper surface extending about the concave articulating surface and generally opposite to the glenoid bone contacting surface, the upper surface having an upper edge defining a second plane, the second plane not parallel to the first plane; and
a drill guide configured to guide a drill in forming a bore in a scapula to receive the first offset peg.

2. The kit of claim 1, wherein the drill guide comprises:
a generally flat drill guide bone contacting surface defining a third plane;
a drill guide peg extending away from a bottom portion of the drill guide and defining a drill guide peg axis, the drill guide peg axis forming an angle other than 90 degrees with the third plane when viewed from a side plan view; and
a first drill guide hole extending upwardly from a bottom surface of the drill guide and defining a first drill guide hole axis, the first drill guide hole axis forming an angle other than 90 degrees with the third plane when viewed from a side plan view, wherein a first minimum angle defined by the drill guide peg axis and the third plane is the same as a second minimum angle defined by the first drill guide hole axis and the third plane.

3. The kit of claim 2, the retroversion glenoid component further comprising:
a center peg extending away from the glenoid bone contacting surface and defining a center peg axis, the center peg axis forming an angle other than 90 degrees with the first plane when viewed from a side plan view, wherein a third minimum angle defined by the center peg axis and the first plane is the same as the first minimum angle.

4. The kit of claim 3, wherein:
the first offset peg defines a first offset peg axis, the first offset peg axis forming an angle other than 90 degrees with the first plane when viewed from a side plan view;
the retroversion glenoid component includes a second offset peg, the second offset peg defining a second offset peg axis parallel to the first offset peg axis;
the retroversion glenoid component includes a third offset peg, the third offset peg defining a third offset peg axis parallel to the first offset peg axis;
the drill guide includes a second drill guide hole defining a second drill guide hole axis parallel to the first drill guide hole axis;
the drill guide includes a third drill guide hole defining a third drill guide hole axis parallel to the third drill guide hole axis; and
a fourth minimum angle defined by the first offset peg axis and the first plane is the same as the first minimum angle.

5. The kit of claim 3, further comprising:
a pin placement guide, the pin placement guide including
a bone contacting surface defining a fourth plane,
a first pin guide hole extending upwardly from a bottom portion of the pin placement guide and defining a first pin guide hole axis, the first pin guide hole axis perpendicular to the fourth plane, and
a second pin guide hole extending upwardly from the bottom portion of the pin placement guide and defining a second pin guide hole axis, the second pin guide hole axis forming an angle other than 90 degrees with the fourth plane when viewed from a side plan view.

6. The kit of claim 5 wherein:
a fifth minimum angle defined by the second pin guide hole axis and the fourth plane is the same as the first minimum angle.

7. The kit of claim 3, wherein:
the glenoid bone contacting surface defines a circular periphery;
the center peg is centered within the circular periphery; and
a nadir of the concave articulating surface is located on the center peg axis.

8. The kit of claim 3, wherein:
the first offset peg defines a first offset peg axis;
the third minimum angle, the center peg axis, and the first offset peg axis are coplanar;
the first minimum angle, the drill guide peg axis, and the first drill guide hole axis are coplanar;
the center peg axis and the first offset peg axis define a first minimum distance therebetween;
the drill guide peg axis and the first drill guide hole axis define a second minimum distance therebetween; and
the first minimum distance is equal to the second minimum distance.

9. The kit of claim 8, wherein:
the retroversion glenoid component includes a second offset peg, the second offset peg defining a second offset peg axis parallel to the first offset peg axis;
the retroversion glenoid component includes a third offset peg, the third offset peg defining a third offset peg axis parallel to the first offset peg axis;
the center peg axis is located between the second offset peg axis and the third offset peg axis;
a fourth plane is perpendicular to the center peg axis;
a first intersection of the second offset peg axis with the fourth plane and a second intersection of the third offset peg axis with the fourth plane are equidistant from a third intersection of the first offset peg axis with the fourth plane;
the drill guide includes a second drill guide hole defining a second drill guide hole axis parallel to the first drill guide hole axis;
the drill guide includes a third drill guide hole defining a third drill guide hole axis parallel to the third drill guide hole axis;
the drill guide peg axis is located between the second drill guide hole axis and the third drill guide hole axis;
a fifth plane is perpendicular to the drill guide peg axis; and
a fourth intersection of the second drill guide hole axis with the fifth plane and a fifth intersection of the third drill guide hole axis with the fifth plane are equidistant from a sixth intersection of the first drill guide hole axis with the fifth plane.

10. A kit for implanting a glenoid component comprising:
a retroversion glenoid component including a generally flat glenoid bone contacting surface defining a first plane, a glenoid peg extending away from the glenoid bone contacting surface and defining a glenoid peg axis, the glenoid peg axis forming an angle other than 90 degrees with the first plane when viewed from a side plan view, and a concave articulating surface; and
a drill guide configured to guide a drill in forming a bore in a scapula, the drill guide including a generally flat drill guide bone contacting surface defining a second plane and a drill guide peg extending away from a bottom portion of the drill guide and defining a drill guide peg axis, the drill guide peg axis forming an angle other than 90 degrees with the second plane when viewed from a side plan view, wherein a first minimum angle defined by the glenoid peg axis and the first plane is the same as a second minimum angle defined by the drill guide peg axis and the second plane.

11. The kit of claim 10, wherein the drill guide comprises:
a first drill guide hole extending upwardly from a bottom surface of the drill guide and defining a first drill guide hole axis, the first drill guide hole axis parallel to the drill guide peg axis.

12. The kit of claim 11, wherein:
the retroversion glenoid component further includes a first offset peg extending away from the glenoid bone contacting surface and defining a first offset peg axis;
the first minimum angle, the glenoid peg axis, and the first offset peg axis are coplanar;
the glenoid peg axis and the first offset peg axis define a first minimum distance therebetween;
the second minimum angle, the drill guide peg axis, and the first drill guide hole axis are coplanar;
the drill guide peg axis and the first drill guide hole axis define a second minimum distance therebetween; and
the first minimum distance is equal to the second minimum distance.

13. The kit of claim 12, wherein:
the retroversion glenoid component includes a second offset peg, the second offset peg defining a second offset peg axis parallel to the first offset peg axis;
the retroversion glenoid component includes a third offset peg, the third offset peg defining a third offset peg axis parallel to the first offset peg axis;
the drill guide includes a second drill guide hole defining a second drill guide hole axis parallel to the first drill guide hole axis; and
the drill guide includes a third drill guide hole defining a third drill guide hole axis parallel to the third drill guide hole axis.

14. The kit of claim 13, wherein:
the glenoid peg axis is located between the second offset peg axis and the third offset peg axis;
a third plane is perpendicular to the center peg axis;
a first intersection of the second offset peg axis with the third plane and a second intersection of the third offset peg axis with the third plane are equidistant from a third intersection of the first offset peg axis with the third plane;
the drill guide peg axis is located between the second drill guide hole axis and the third drill guide hole axis;
a fourth plane is perpendicular to the drill guide peg axis; and
a fourth intersection of the second drill guide hole axis with the fourth plane and a fifth intersection of the third drill guide hole axis with the fourth plane are equidistant from a sixth intersection of the first drill guide hole axis with the fourth plane.

15. The kit of claim 12, further comprising:
a pin placement guide, the pin placement guide including
a bone contacting surface defining a third plane,
a first pin guide hole extending upwardly from a bottom portion of the pin placement guide and defining a first pin guide hole axis, the first pin guide hole axis perpendicular to the third plane, and
a second pin guide hole extending upwardly from the bottom portion of the pin placement guide and defining a second pin guide hole axis, the second pin guide hole axis forming an angle other than 90 degrees with the third plane when viewed from a side plan view.

16. The kit of claim 15 wherein:
a third minimum angle defined by the second pin guide hole axis and the third plane is the same as the first minimum angle.

17. The kit of claim 16, wherein:
the glenoid bone contacting surface defines a circular periphery;
the glenoid peg is centered within the circular periphery; and
a nadir of the concave articulating surface is located on the glenoid peg axis.

18. A kit for implanting a glenoid component comprising:
a retroversion glenoid component including (i) a concave articulating surface with an upper surface having an upper edge extending about the concave articulating surface and defining a first plane, (ii) a generally flat glenoid bone contacting surface generally opposite to the concave articulating surface and coextensive with the concave articulating surface when the concave articulating surface and generally flat glenoid bone contacting surface are projected onto the first plane, the generally flat glenoid bone contacting surface defining a second plane which is not parallel to the first plane, and (iii) a first offset peg extending away from the glenoid bone contacting surface at an angle other than 90 degrees when viewed from a side plan view; and
a drill guide configured to guide a drill in forming a bore in a scapula to receive the first offset peg.

19. The kit of claim 18, wherein the drill guide comprises:
a generally flat drill guide bone contacting surface defining a third plane;
a drill guide peg extending away from a bottom portion of the drill guide and defining a drill guide peg axis, the drill guide peg axis forming an angle other than 90 degrees with the third plane when viewed from a side plan view; and
a first drill guide hole extending upwardly from a bottom surface of the drill guide and defining a first drill guide hole axis, the first drill guide hole axis forming an angle other than 90 degrees with the third plane when viewed from a side plan view, wherein a first minimum angle defined by the drill guide peg axis and the third plane is the same as a second minimum angle defined by the first drill guide hole axis and the third plane.

20. The kit of claim 19, the retroversion glenoid component further comprising:
a center peg extending away from the glenoid bone contacting surface and defining a center peg axis, the center peg axis forming an angle other than 90 degrees with the second plane when viewed from a side plan view, wherein a third minimum angle defined by the center peg axis and the second plane is the same as the first minimum angle.

* * * * *